United States Patent [19]
Lin et al.

[11] Patent Number: 6,010,662
[45] Date of Patent: Jan. 4, 2000

[54] TWO-STEP STERILIZATION PROCESS USING LIQUID STERILANT

[75] Inventors: Szu-Min Lin, Laguna Hills; Paul Taylor Jacobs, Trabuco Canyon, both of Calif.

[73] Assignee: Ethicon, Inc., Somerville, N.J.

[21] Appl. No.: 09/099,591

[22] Filed: Jun. 18, 1998

[51] Int. Cl.[7] ................................ A61L 2/20; A61L 2/08
[52] U.S. Cl. .............................. 422/33; 422/22; 422/292
[58] Field of Search .................... 422/28, 33, 22, 422/292, 186.05, 186.3

[56] References Cited

U.S. PATENT DOCUMENTS

| | | | |
|---|---|---|---|
| 4,169,124 | 9/1979 | Forstrom et al. | 422/33 |
| 5,286,448 | 2/1994 | Childers | 422/28 |
| 5,869,000 | 2/1999 | DeCato | 422/33 |

*Primary Examiner*—Elizabeth McKane
*Attorney, Agent, or Firm*—Andrew Farmer

[57] ABSTRACT

A method sterilizes a device having a diffusion restricted area and a non-diffusion restricted area. The method includes the steps of vaporizing a first solution of hydrogen peroxide within the diffusion restricted area and vaporizing a second solution of hydrogen peroxide outside of the diffusion restricted area, with the first solution having a lower concentration of hydrogen peroxide than the second solution.

19 Claims, 3 Drawing Sheets

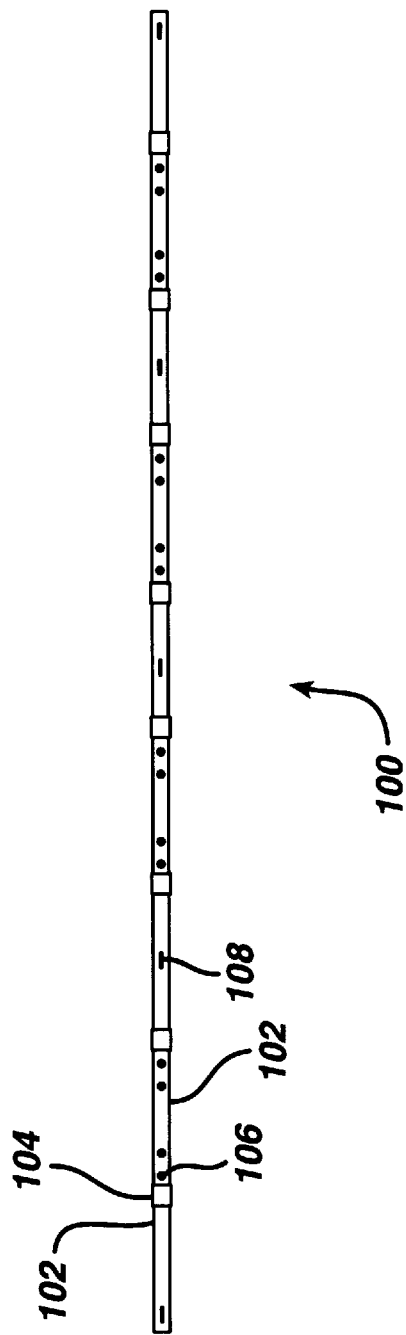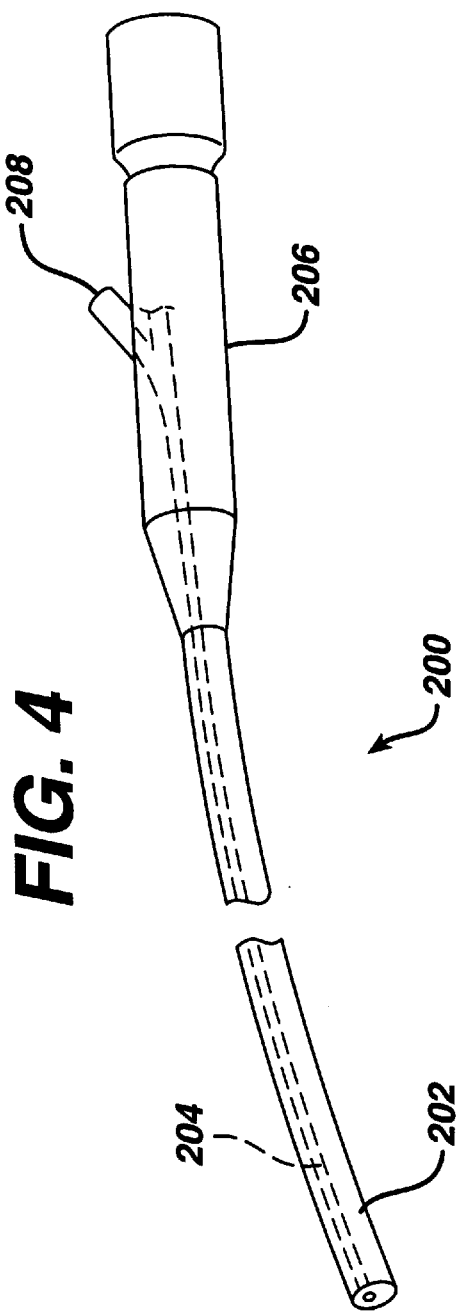

TWO-STEP STERILIZATION PROCESS USING LIQUID STERILANT

FIELD OF THE INVENTION

The present invention relates to a process for sterilization of medical instruments using a liquid sterilant. More particularly, the invention relates to a process in which sterilization is achieved by vaporizing at least two different solutions of hydrogen peroxide having different concentrations.

BACKGROUND OF THE INVENTION

Medical instruments have traditionally been sterilized using either heat, such as is provided by steam, or a chemical, such as formaldehyde or ethylene oxide in the gas or vapor state. Each of these methods has its drawbacks. Many medical devices such as fiberoptic devices, endoscopes, power tools, etc., are sensitive to heat, moisture or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization time undesirably long.

Sterilization using liquid hydrogen peroxide solution has been found to require high concentrations of sterilant, extended exposure time and/or elevated temperatures. However, sterilization using hydrogen peroxide vapor has been shown to have some advantages over other chemical sterilization processes (see, e.g., U.S. Pat. Nos. 4,169,123 and 4,169,124). The combination of hydrogen peroxide with a plasma provides certain additional advantages, as disclosed in U.S. Pat. No. 4,643,876. The sterilization of articles containing diffusion-restricted areas, such as long narrow lumens, presents a special challenge. Methods that use hydrogen peroxide vapor that has been generated from an aqueous solution of hydrogen peroxide have certain disadvantages. One disadvantage is that because water has a higher vapor pressure than hydrogen peroxide, it will vaporize faster. Another disadvantage is that because of its lower molecular weight, water will diffuse faster than hydrogen peroxide in the vapor state. Because of these physical properties, when an aqueous solution of hydrogen peroxide is vaporized in the area surrounding the items to be sterilized, the water reaches the items first and in higher concentration. The water vapor therefore becomes a barrier to the penetration of hydrogen peroxide vapor into diffusion-restricted areas, such as small crevices and long narrow lumens. This problem cannot be addressed by removing water from the aqueous solution and using more concentrated hydrogen peroxide because, among other reasons, hydrogen peroxide solutions greater than 65% by weight can be hazardous due to their oxidizing potential.

U.S. Pat. No. 4,952,370 discloses a sterilization process in which aqueous hydrogen peroxide vapor is first condensed on the article to be sterilized, followed by application of a vacuum to the sterilization chamber to evaporate the water and hydrogen peroxide from the article. This method is suitable for surface sterilization, but not for sterilization of diffusion-restricted areas such as long narrow lumens because it depends on the diffusion of hydrogen peroxide vapor into the lumen to effect sterilization.

U.S. Pat. No. 4,943,414 discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the existing pressure differential, increasing the sterilization rate for lumens, but has the disadvantage that the vessel needs to be attached to each lumen to be sterilized. In addition, water is vaporized faster and precedes the hydrogen peroxide vapor into the lumen.

In U.S. Pat. No. 5,492,672, there is disclosed a process for sterilizing narrow lumens. This process uses a multicomponent sterilant vapor and requires successive alternating periods of flow of sterilant vapor and discontinuance of such flow. A complex apparatus is used to accomplish the method. Because flow through of vapor is used, closed end lumens are not readily sterilized in the process.

Thus, there remains a need for a simple and effective method of vapor sterilization of articles having areas where diffusion of these vapors is restricted, such as long narrow lumens.

SUMMARY OF THE INVENTION

A method for sterilizing a device having a diffusion restricted area and a non-diffusion restricted area according to the present invention comprises the steps of: contacting the diffusion restricted area with a first liquid sterilant solution of a first concentration; placing the device in a sterilization chamber; introducing a second liquid sterilant solution of a second concentration into the sterilization chamber exterior of the diffusion restricted area, the second concentration being greater than the first concentration; lowering the pressure of the chamber to vaporize the first and second liquid sterilant solutions and sterilize the diffusion restricted area and the non-diffusion restricted area of the instrument.

Preferably, both of the first and second liquid sterilant solutions comprise hydrogen peroxide and water, such as a pure hydrogen peroxide and water solution or a paracetic acid solution. Preferably, the concentration of hydrogen peroxide in the first liquid sterilant solution is less than 20 percent, and more preferably is less than 10 percent. The concentration of hydrogen peroxide in the second liquid sterilant solution can be greater than 40 percent, and can be greater than 55 percent.

The pressure in the chamber can first lowered to a first pressure range for preferentially vaporizing the second liquid sterilant solution and then further lowered to a second lower pressure range for vaporizing the first liquid sterilant solution. Preferably, the pressure in the chamber is lowered below the vapor pressure of the second liquid sterilant solution, and more preferably to 20 Torr or less.

One particularly suitable set of parameters contemplates that the concentration of hydrogen peroxide in the first liquid sterilant solution is less than 10 percent, the concentration of hydrogen peroxide in the second liquid sterilant solution is greater than 45 percent. Preferably, the first and second concentrations are selected to allow the lowering of the chamber to a single pressure range which vaporizes the first liquid sterilant solution and second liquid sterilant solution simultaneously.

The method is particularly suited to sterilizing devices such as medical instruments where the diffusion restricted area comprises a lumen therein.

The step of contacting the diffusion restricted area with a liquid sterilant solution may comprise the step of condensing the liquid sterilant solution from a vapor inside the diffusion restricted area. Alternatively, it may comprise the step of flowing a mist of the liquid sterilant solution into the diffusion restricted area.

Preferably, an air flow is passed through the sterilization chamber to remove excess of the first liquid sterilant after the steps of contacting the diffusion restricted area with a first liquid sterilant solution and placing the device in a sterilization chamber, but prior to the step of lowering the pressure to vaporize the first and second liquid sterilant solutions.

The hydrogen peroxide can be excited into a plasma after the step of vaporizing. Also, the chamber pressure can be allowed to rise, such as through the admission of air into the chamber, after vaporizing the first liquid sterilant solution whereupon the pressure is lowered and the second liquid sterilant solution is introduced into the chamber.

BRIEF DESCRIPTION OF THE DRAWINGS

FIG. 3 is a schematic diagram of a test lumen used in the examples.

FIG. 4 is a perspective view of an endoscope for sterilization using the process of the invention.

DETAILED DESCRIPTION OF THE PREFERRED EMBODIMENTS

Introduction

Sterilizing the inside of lumened devices has always posed a challenge to sterilization systems. Applicants' copending U.S. application Ser. No. 08/628,965, the entire contents of which are hereby incorporated by reference, discloses a method of hydrogen peroxide vapor sterilization of diffusion-restricted environments, such as long narrow lumens, at pressures less than the vapor pressure of hydrogen peroxide by pretreating the article to be sterilized with a dilute solution of hydrogen peroxide prior to exposure to a vacuum. One possible approach is to create a diffusion restricted vacuum chamber and to vaporize liquid sterilant within the chamber. Depending upon the size of the diffusion restricted area and the pressure at which the sterilization is performed, it may take too long to evacuate the system. Achieving rapid sterilization of lumened devices or other diffusion restricted articles at low temperatures and low concentrations of sterilant represents an even greater challenge.

Figure 1:
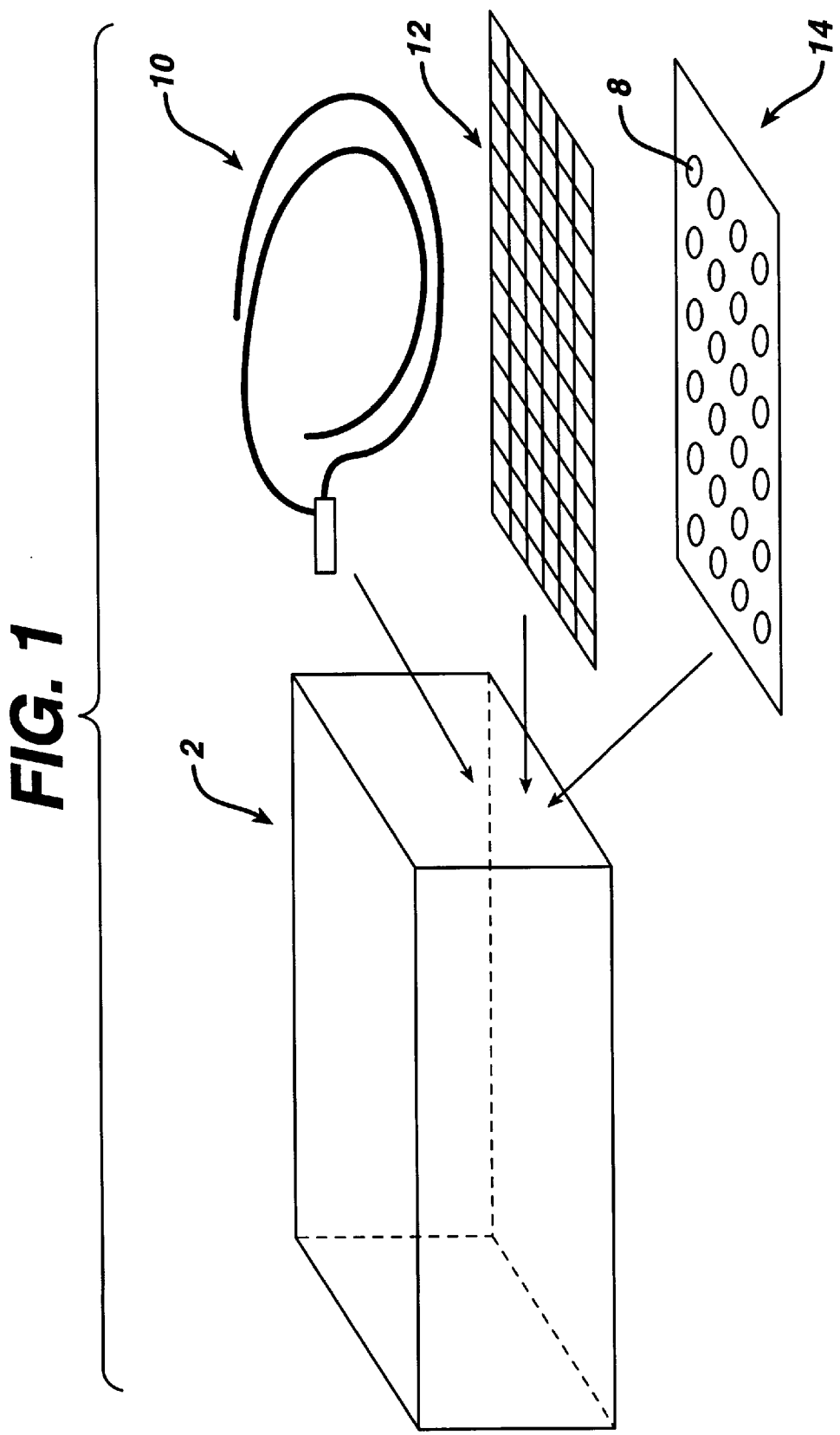
FIG. 1 is a schematic diagram of a chamber and accessories suitable for use in the hydrogen peroxide sterilization process of the invention.
Figure 2:
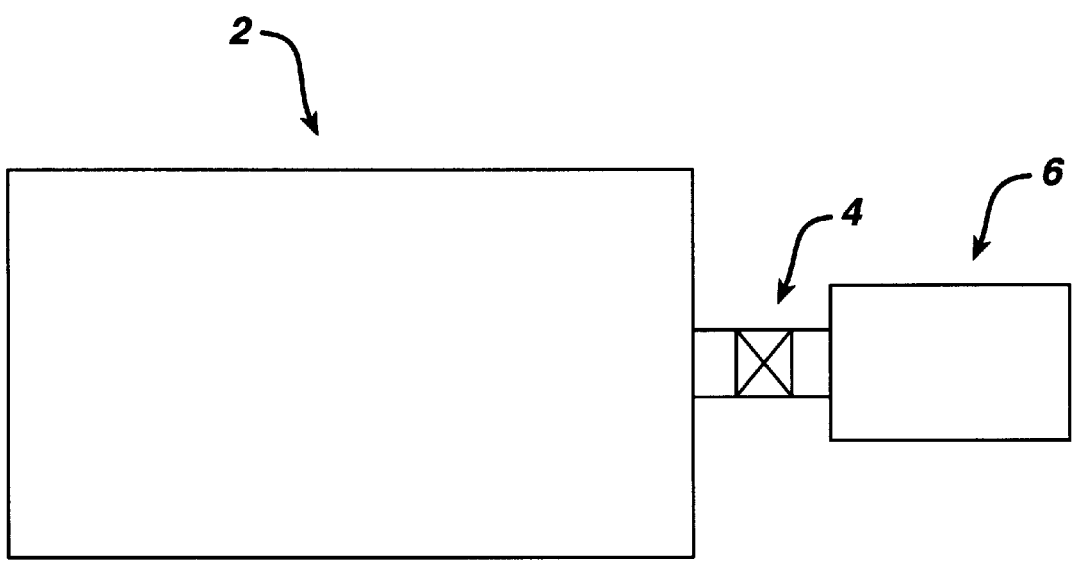
FIG. 2 is a schematic diagram of a chamber, pump and throttle valve for use in the hydrogen peroxide sterilization process of the invention.

An apparatus useful in the process of the present invention is shown schematically in FIGS. 1 and 2 and comprises a chamber 2, a throttle valve 4 and a pump 6. In FIG. 2, the chamber 2 is attached to the pump 6 by the throttle valve 4. The valve 4 can be controlled either automatically to maintain the pressure or manually to maintain a constant pump-down rate. In the automatic mode of operation, the throttle valve 4 opens based on the pressure in the chamber via a pressure transducer and valve controller. Such valves are commercially available from, for example, MKS (Andover, MD). In this process a dilute, aqueous solutions of hydrogen peroxide is placed in wells 8 as shown in FIG. 1. As the pressure in the sterilization chamber 2 is reduced, the hydrogen peroxide vaporizes and contacts the surface to be sterilized (i.e., colonoscope 10 in FIG. 1) which is placed on metal grid 12 which rests on tray 14. In a preferred embodiment, the tray can be configured with a plurality of wells designed to retain a known volume of liquid sterilant. In one embodiment, the volume of sterilization chamber 2 is about 18.5 liters and its dimensions are about 22" (55.9 cm)×4.25" (10.8 cm)×12" (30.5 cm).

Hydrogen peroxide can be introduced into the chamber as a liquid. In a preferred embodiment, hydrogen peroxide is introduced as a vapor and the chamber parameters are changed so that the vapor condenses as a liquid on the surface of an article to be sterilized. Such changes include increasing the pressure.

The aqueous solutions of hydrogen peroxide can be relatively dilute, e.g. as low as 1–6% peroxide by weight, since sterilization is not achieved through contact with the hydrogen peroxide solution, but rather is achieved at low temperatures and in short periods of time upon exposure to hydrogen peroxide under vacuum. The method of the present invention is particularly effective with articles having inaccessible or hard-to-reach places. Such articles include long, narrow lumens, hinges and other articles having spaces where diffusion of vapors is restricted. Although hydrogen peroxide is used in the examples described herein, the use of other liquid sterilants are also contemplated. Preferred sterilants have vapor pressures lower than the vapor pressure of the solvent in which they are provided. Such sterilants include, for example, aqueous peracetic acid solution and aqueous glutaraldehyde solution.

At the end of the process, deep vacuum can be used to remove residual sterilant. A plasma can also be used to remove residual sterilant and to enhance sterilization efficacy.

The method of the present invention is described below. This invention results from our discovery that different pressures are optimally used to sterilize the exterior of diffusion-restricted articles than the interior thereof. As used herein, a "diffusion-restricted" area refers to any one or more of the following properties: (1) the ability of the area of an article placed within the sterilization system of the present invention to retain 0.17 mg/L or more hydrogen peroxide solution after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the hydrogen peroxide solution placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

Sterilization of Exterior

To evaluate the sterilization efficacy of hydrogen peroxide vapor generated from 6% hydrogen peroxide solution at different pressures on the exterior surface of an article to be sterilized, a biological challenge consisting of 2.3×10$^6$ Bacillus stearothermophilus (Bst) spores was placed in uncovered petri dishes or on the insertion tube of a CF10 colonoscope (Olympus). Four scalpel blades were used per cycle, two in the petri dish and two on the colonoscope. The temperature of the chamber was 45° C. The pressure varied from 200 torr to 1 torr by controlling the valve in automatic mode. 2400 µl in 50 drops of 6% peroxide were used as shown in FIG. 1. The blades were removed and tested for sterility. The results of this testing is present in Table 1 as a ratio of the number of inoculated blades which remain contaminated after treatment over the number of inoculated blades tested.

TABLE 1

Sporicidal Activity (positives/samples)

| Pressure (torr) | 5 minutes | | 10 minutes | |
|---|---|---|---|---|
| | In uncovered petri dish | On insertion tube of colonoscope | In uncovered petri dish | On insertion tube of colonoscope |
| 200 | 1/2 | 2/2 | 0/2 | 0/2 |
| 175 | 0/2 | 2/2 | 0/2 | 0/2 |
| 150 | 0/2 | 2/2 | 0/2 | 0/2 |
| 125 | 0/2 | 2/2 | 0/2 | 0/2 |
| 100 | 0/2 | 2/2 | 0/2 | 0/2 |
| 90 | 0/2 | 2/2 | 0/2 | 0/2 |
| 80 | 0/2 | 1/2 | 0/2 | 0/2 |
| 70 | 0/2 | 1/2 | 0/2 | 0/2 |
| 60 | 0/2 | 1/2 | 0/2 | 0/2 |
| 50 | 0/2 | 0/2 | 0/2 | 0/2 |
| 40 | 0/2 | 0/2 | 0/2 | 0/2 |
| 30 | 0/2 | 2/2 | 0/2 | 1/2 |
| 25 | 0/2 | 2/2 | 0/2 | 2/2 |
| 20 | 0/2 | 2/2 | 0/2 | 2/2 |
| 15 | 0/2 | 2/2 | 0/2 | 2/2 |
| 10 | 1/2 | 2/2 | 0/2 | 2/2 |
| 5 | 2/2 | 2/2 | 2/2 | 2/2 |
| 1 | 2/2 | 2/2 | 2/2 | 2/2 |

As shown in the table, if the pressure is too low (5 torr or less), the majority of peroxide vaporizes immediately and is removed during evacuation. Thus, less peroxide is available to sterilize the blades. Under the test conditions, the optimal pressure for the 5 minute time period is about 40–50 torr. With 10 minutes exposure, sterilization can be achieved at pressures up to about 200 torr. It appears to take longer to vaporize peroxide at higher pressures. The vapor pressure of hydrogen peroxide under these conditions is about 80–90 torr, thus sterilization can be achieved at pressures higher than the vapor pressure of hydrogen peroxide. The blades on the insertion tube may simulate the most difficult areas to be sterilized in the system because the insertion tube tends to absorb peroxide, leaving less available for sterilization of the blades placed thereon.

The exterior of the article can also be effectively sterilized when performed at atmospheric pressure. In order to confirm this, two scalpel blades were each inoculated with $2.3 \times 10^6$ Bst spores (two SS blades per cycle), placed in uncovered petri dishes, placed in the chamber and exposed to 48 drops×50 µl/drop of 6% hydrogen peroxide at 60° C. at atmospheric pressure. Both blades were sterilized after 30 minutes exposure under these conditions.

Interior Sterilization

To determine the efficacy of the liquid/vapor process on the inside surfaces of an article to be sterilized, polytetrafluoroethylene (PTFE) lumens containing Bst spores were used. The effects of lumen length, internal diameter and amount of peroxide in the lumen on sterilization were investigated. PTFE lumens were loaded with a stainless steel coupon at the center of the lumen. A stainless steel coupon consists of a piece of scalpel blade cut from the proximal end of the blade having dimensions of about 2 mm×4 mm. Sterilization parameters were: 45° C., 48 drops×50 µl per drop 6% peroxide; $8.8 \times 10^5$ Bst per coupon and 10 minute exposure. Peroxide was either absent from the lumen or present about 1 cm or more away from the coupon on both sides thereof. The length of the lumen was 20, 50, 100 or 200 cm. The internal diameter of the lumen was 2.38 or 4.76 mm. The results for the lumens not containing additional peroxide in the lumen are shown in

TABLE 2A

| Length of Lumen | I.D. of Lumen | Amount of peroxide in the lumen | Presence of Spores | | | | |
|---|---|---|---|---|---|---|---|
| | | | 50 torr | 30 torr | 10 torr | 5 torr | 1 torr |
| 20 cm | 2.38 mm | 0 | − | − | + | + | + |
| | 4.76 mm | 0 | − | − | + | + | + |
| 50 cm | 2.38 mm | 0 | + | + | + | + | + |
| | 4.76 mm | 0 | + | + | + | + | + |
| 100 cm | 2.38 mm | 0 | + | + | + | + | + |
| | 4.76 mm | 0 | + | + | + | + | + |

Because no peroxide was present in the lumen, the only source of peroxide for sterilization of the lumen was from outside the lumen, such as from wells placed in the sterilization chamber. Thus, diffusion of the peroxide vapor from outside to the inside of the device is required. As shown in Table 2A, these parameters resulted in sterilization of only the shortest lumen tested (20 cm), and only at the highest pressures (30 and 50 torr). Because peroxide vapor is diffusing from outside to inside, when the pressure is too low, very little peroxide is present because most is removed from the chamber at the lower pressures. Without hydrogen peroxide in the lumen, only short lumens can be sterilized at high pressure because the flow of peroxide vapor is from outside to inside. The center of the longer lumens could not be reached by the peroxide vapor diffusing in from the outside source.

TABLE 2B

| Length of Lumen | I.D. of Lumen | Amount of peroxide in the lumen | Presence of Spores | | | | |
|---|---|---|---|---|---|---|---|
| | | | 50 torr | 30 torr | 10 torr | 5 torr | 1 torr |
| 20 cm | 2.38 mm | 2 × 5 µL | + | + | − | − | + |
| | 4.76 mm | 2 × 5 µL | − | + | − | − | + |
| 50 cm | 2.38 mm | 2 × 5 µL | + | − | − | − | + |
| | 4.76 mm | 2 × 5 µL | − | − | − | − | + |
| 100 cm | 2.38 mm | 2 × 2.5 µL | + | + | − | − | − |
| | mm | 2 × 5 µL | + | + | − | − | − |
| | 4.76 mm | 2 × 2.5 µL | − | − | − | −. | − |
| | mm | 2 × 5 µL | + | + | − | − | − |
| 200 cm | 2.38 mm | 2 × 2.5 µL | + | − | | | |
| | mm | 2 × 5 µL | + | + | − | − | − |
| | 4.76 mm | 2 × 2.5 µL | + | − | − | − | − |
| | mm | 2 × 5 µL | + | + | − | − | − |

The results for the lumens containing additional peroxide are shown in Table 2B. The peroxide was placed about 1 cm away from the coupon on both sides thereof. This method was much more effective in sterilizing the coupons contained within the lumens. It is noted that the 20 cm lumen at 30 and 50 torr contained spores in the 2.38 mm I.D. lumen while the previous table shows that no spores were present under these conditions. While not wishing to be bound by any particular explanation of these results, it is believed that these results are due to the presence of additional water vapor which prevents peroxide from diffusing from outside to inside. The 4.76 mm tube is large enough that the peroxide is not prevented from diffusing from outside to inside. Sterilization can occur at 50 torr because the lumen is large enough. Pressures of 5 torr and 10 torr consistently provide good efficacy results with hydrogen peroxide in the lumen with the test samples in the lumen. Thus, under the test conditions at 45° C., the optimal pressures for hydrogen peroxide sterilization of the interior of an article (5–10 torr) is different from those for sterilization of the exterior of an article (40–50 torr).

Another experiment examined the effects of exposure time, lumen I.D., amount of peroxide and distance between peroxide and the coupon. The pressure was 5 torr and the length of the Teflon lumen was 200 cm.

TABLE 2C

| Exposure Time | I.D. of Lumen | Amount of Peroxide in the Lumen | Presence of Spores | | |
|---|---|---|---|---|---|
| | | | 1 cm away | 10 cm away | 20 cm away |
| 5 min | 2.38 mm | 2 × 2.5 μL | – | – | – |
| | | 2 × 5.0 μL | – | + | + |
| | 4.76 mm | 2 × 2.5 μL | – | – | – |
| | | 2 × 5.0 μL | – | – | – |
| 10 min | 2.38 mm | 2 × 2.5 μL | – | – | – |
| | | 2 × 5.0 μL | – | – | – |
| | 4.76 mm | 2 × 2.5 μL | – | – | – |
| | | 2 × 5.0 μL | – | – | – |

As shown in Table 2C, the peroxide source could be placed 1 cm, 20 cm, or 20 cm from the coupon and still result in effective sterilization thereof. The one exception was the 5 minute exposure time, 2.38 mm I.D., 2×5.0 μl peroxide. This may be due to vaporization of water which impedes access of peroxide inside the narrower lumen. Small lumens require longer times to vaporize more peroxide solution.

Two-step process

In view of the different optimal pressures for sterilizing the inside and outside of diffusion-restricted articles, we have developed a two-step process for rapidly sterilizing both the interior and exterior of articles. Depending on the temperature, concentration and amount of hydrogen peroxide, the first step is performed at a first pressure range which can be as high as atmospheric pressure and as low as about 20 torr. The second pressure range is typically between 1 and about 30 torr, preferably between about 5 and 10 torr. In a preferred embodiment, upon reaching the first or second pressure ranges in the two-step process, the valve between the pump and the chamber is closed to allow peroxide vaporization which increases the pressure. In another embodiment, the first or second pressure ranges occur through gradual evacuation of the chamber starting at a pressure at a higher end of the range (i.e. the first and second pressures are not linearly maintained). Optionally, a final evacuation step may be rapidly performed to remove condensed residual hydrogen peroxide at a very low pressure (0.1–5 torr). A plasma can also be used for this purpose or to help in the sterilization process.

During the sterilization at each of the first and second pressure ranges, the valve to the chamber can be set to control the pressure of the chamber to remain constant. Alternatively, and more preferably, the valve can be closed, so as to permit the pressure within the chamber to increase as a result of vaporization of the sterilant. Allowing the pressure to so rise will permit additional sterilant vapor to contact the article to be sterilized. In still another alternative, the valve can be set to continue decreasing the pressure of the chamber, albeit at a slower rate.

Alternatively, rather than use a single concentration of hydrogen peroxide solution and a different vaporization pressure for preferentially vaporizing the hydrogen peroxide solution in interior and exterior of the lumens, one can employ a lower concentration hydrogen peroxide solution within the lumens and a higher concentration hydrogen peroxide solution exterior of the lumens, preferably with a single vaporization pressure. For instance, a 50 percent solution of hydrogen peroxide may be placed inside the chamber exterior of the lumen or diffusion restricted area and a 6 percent solution of hydrogen peroxide may be placed into the lumen and diffusion restricted area. A vaporization pressure of 10 Torr produces excellent results with these concentrations. Employing different concentrations significantly speeds the vaporization portion of the sterilization cycle, even over the dual pressure method outlined above, to reduce the overall time necessary to effect sterilization of the instruments. Of course, more than one pressure can be used to vaporize the different concentrations of sterilant or the pumpdown rate at which the pressure in the chamber can be controlled so as to optimize the vaporization of hydrogen peroxide with minimal losses while minimizing the time to vaporize the sterilant inside and outside of the diffusion restricted area.

The following examples illustrate the effectiveness of the method in achieving rapid sterilization of long narrow lumens.

Tests were performed to determine the effects of pressure, exposure time and volume of hydrogen peroxide on the sterilization efficacy of an Olympus brand model CF10 colonoscope insertion tube. A biological indicator (BI) comprising a stainless steel blade inoculated with spores of *B. stearothermophilus* was placed atop the insertion tube of the colonoscope. The colonoscope was placed on an aluminum tray and 1,000 μL of a 50% hydrogen peroxide/water solution was placed on the tray. The tray, hydrogen peroxide solution and colonoscope were placed into a chamber having a temperature of 45° C. and the pressure of the chamber was lowered to vaporize the hydrogen peroxide solution.

TABLE 3A

Effect of pressure, exposure time and volume of peroxide

| | Sporicidal Activity (positives/samples) | | | |
|---|---|---|---|---|
| Pressure | 1000 μL | | 1100 μL | |
| (torr) | 5 min. | 10 min. | 5 min. | 10 min. |
| 50 | 2/2 | 2/2 | 2/2 | 2/2 |
| 20 | 2/2 | 0/2 | 1/2 | 0/2 |
| 10 | 0/2 | 0/2 | 0/2 | 0/2 |
| 5 | 2/2 | 1/2 | 1/2 | 0/2 |
| 1 | 2/2 | 2/2 | 2/2 | 2/2 |

Test conditions:
Chamber temperature: 45° C.
Location of BI: on insertion tube of colonoscope
BI: $1.3 \times 10^6$ *B. stearothermophilus* on SS blade
Concentration of peroxide: 50%
Distribution of peroxide: one drop on aluminum pan

TABLE 3B

Effect of pressure, exposure time and size of peroxide drop

| | Sporicidal Activity (positives/samples) | | | |
|---|---|---|---|---|
| Pressure | one drop w/1000 uL/drop | | 20 drops w/50 uL/drop | |
| (torr) | 5 min. | 10 min. | 5 min. | 10 min. |
| 50 | 2/2 | 2/2 | 2/2 | 0/2 |
| 20 | 2/2 | 0/2 | 0/2 | 0/2 |
| 10 | 0/2 | 0/2 | 0/2 | 0/2 |
| 5 | 2/2 | 1/2 | 2/2 | 1/2 |
| 1 | 2/2 | 2/2 | 2/2 | 2/2 |

Test conditions:
Chamber temperature: 45° C.
Location of BI: on insertion tube of colonoscope
BI: 1.3 × 10$^6$ *B. stearothermophilus* on SS blade
Concentration of peroxide: 50%
Volume of peroxide: 1000 μL on aluminum pan

TABLE 3C

Effect of pressure, exposure temperature and size of peroxide drop

| | Sporicidal Activity (positives/samples) | | | |
|---|---|---|---|---|
| Pressure | 45° C. | | 50° C. | |
| (torr) | 1000 uL/drop | 50 uL/drop | 1000 uL/drop | 50 uL/drop |
| 50 | 2/2 | 2/2 | 2/2 | 0/2 |
| 20 | 2/2 | 0/2 | 1/2 | 0/2 |
| 10 | 0/2 | 0/2 | 0/2 | 0/2 |
| 5 | 2/2 | 2/2 | 1/2 | 2/2 |
| 1 | 2/2 | 2/2 | 2/2 | 2/2 |

Test conditions:
Location of BI: on insertion tube of colonoscope
BI: 1.3 × 10$^6$ *B. stearothermophilus* on SS blade
Concentration of peroxide: 50%
Volume of peroxide: 1000 uL on aluminum pan
Exposure time: 5 minutes These studies show that too low of a pressure can actually hinder the sterilization process. As the atmosphere in the chamber is evacuated to pressures lower than that needed to vaporize the hydrogen peroxide solution, some of the hydrogen peroxide already vaporized will be evacuated from the chamber thereby leaving a lesser amount of hydrogen peroxide vapor for sterilizing the instruments (in this case the exterior of the insertion tube of a colonoscope).

The vapor pressure changes with concentration and higher concentration solutions of hydrogen peroxide require lower pressures to vaporize the hydrogen peroxide therefrom. The diffusion restriction exacerbates this problem in a diffusion restricted environment such as an endoscope lumen such that when using pretreating the interior of the lumen with the same concentration of hydrogen peroxide solution as used exterior of the lumen, to achieve proper vaporization and diffusion of the hydrogen peroxide within the lumen the chamber must be pumped to a lower pressure than would otherwise be desirable. Because of the higher vapor pressure of hydrogen peroxide in lower concentration hydrogen peroxide solutions, a lower concentration hydrogen peroxide solution may be employed within the lumen or diffusion restriction than employed exterior of the lumen. The following table shows the results of a test in which a 50% solution of hydrogen peroxide was used exterior of the lumen and a 6% solution of hydrogen peroxide was used on the interior of a test lumen.

FIG. 3 shows the configuration of the test lumen 100, comprised of 9 segments of Teflon tubing 102, in alternating lengths of 20 cm and 25 cm. The tubing lengths 102 were connected with segments of latex tubing 104. Drops 106 of hydrogen peroxide and biological indicators 108 were distributed within the test lumen 100 as shown.

TABLE 4

Sterilization of interior and exterior with one pressure and two liquid peroxide concentrations

| | Sporicidal Activity (positives/samples) | |
|---|---|---|
| Pressure | | |
| (torr) | Exterior | Interior |
| 10 | 0/2 | 2/5 |

Test conditions:
(A) Exterior
Location of B1: on insertion tube of colonoscope
BI: 1.5 × 10$^6$ *B. stearothermophilus* on SS blade
Concentration of peroxide: 50%
Amount of peroxide: one drop with 1000 uL on aluminum pan
(B) Interior
Location of B1: in 3 mm × 2 m Teflon tube
BI 1.5 × 10$^6$ *B. stearothermophilus* on SS wire
Concentration of peroxide: 6%
Amount of peroxide: 16 drops with 1 uL/drop in the Teflon tubing
(C) Exposure time: 5 minutes
(D) Chamber temperature: 50° C.

In practice, the method of the present invention is quite useful if practiced in connection with an integrated washing and sterilization apparatus for washing and sterilizing lumened instruments such as endoscopes. Washing machines for endoscopes are known to those of skill in the art. One particularly effective method and apparatus is disclosed in Applicants copending application Ser. No. 08/915,922 filed Aug. 21, 1997 and incorporated herein by reference, in which a chamber (not shown here) is divided into two separate compartments by a dividing wall through which passes the insertion tube of an endoscope. A pressure differential between the compartments drives a washing solution through the lumen of the insertion tube. The insertion tube penetrates an opening in the wall which may be openable and closable in some fashion, particularly during the washing process so as to allow easy insertion of the tube and to allow the contact with the insertion tube to be altered so that no portion thereof is completely occluded during the washing process.

FIG. 4 shows in gross the structure of a typical endoscope 200, having an insertion tube 202 for insertion into an animal or human body and a lumen 204 running the length of the insertion tube 202. The insertion tube 202 is attached to a hand-piece 206 which typically, has one or more ports 208 connected to the lumen 204. After the endoscope 200 or other instrument is so washed and rinsed of the washing solution. A pretreatment solution of hydrogen peroxide is applied to the lumen. Many methods may be employed for placing the pretreatment solution of hydrogen peroxide into the lumen 204. It may be flowed through the lumen 204 using the washing equipment just described, with the excess blown out with an air flow. Alternatively, it may be admitted into the chamber 2 as a vapor and condensed onto the endoscope 200 and within its lumen 204. It can be sprayed into the lumen 204. Since only a small quantity is needed, the endoscope may be immersed in a dilute hydrogen peroxide pretreatment solution, such as a 3 or 6% solution of hydrogen peroxide and the excess drained therefrom. The residual solution in the lumen 204 will be sufficient for sterilization. The pretreatment solution may be applied to the lumen 204 either with the endoscope 200 within the chamber 2 or prior to placing the endoscope 200 within the chamber 2.

After pretreating the lumen 204 and placing the endoscope in the chamber 2, it is desirable to purge excess hydrogen peroxide solution from the chamber 2 so as not to dilute the stronger solution to be applied exterior of the lumen 204. This can be accomplished by passing an air flow through the chamber 2. The second stronger solution of hydrogen peroxide -may be in the chamber during this process, but is preferably added after the purging process. The second, stronger hydrogen peroxide solution may be introduced into the chamber 2 in many fashions. It may be placed into a vessel or well therein, or it may be placed in a separate compartment which is placed effectively into the chamber by being placed into fluid communication with the chamber, such as by opening a valve. It may be sprayed or injected therein. If the solution is in fluid communication with the chamber 2 it is considered within the chamber 2. It can be in contact with the endoscope 200, but need not be. Preferably after the second, stronger solution is introduced into the chamber 2, the valve 4 is opened and the pump 6 draws the atmosphere out of the chamber 2 to lower the pressure in the chamber 2. However, the second, stronger solution may be introduced, such as through an injector (not shown) during or after the pumpdown to the desired chamber pressure.

Preferably, the pretreatment solution in the lumen 204 comprises water and less than 10 percent, and preferably 6 percent hydrogen peroxide. Preferably, the second, stronger solution placed in the chamber 2 exterior of the lumen 204 comprises water and about 50% hydrogen peroxide. However, the concentrations of the solutions may be altered to achieve various goals. For instance, the solution exterior of the lumen may be of high or very high concentration, such as 59% or 80%, but such solutions are more expensive and difficult to handle. Good efficacy can be achieved with a 50% solution. One may also vary the concentrations while employing multiple vaporization pressures as described above.

Once the chamber 2 reaches the desired pressure, such as 10 Torr, the valve 4 may be closed, which will thus allow the chamber pressure to rise slightly as the solutions vaporize, or be throttled to maintain a constant pressure. The vaporized hydrogen peroxide is left in contact with the endoscope 200 for a sufficient period of time to sterilize both the exterior of the endoscope 200 and the lumen 204. A plasma may be applied, such as by exciting the hydrogen peroxide molecules with an electromagnetic field, at or near the end of the sterilization process to enhance the efficiency of the sterilization with the added benefit of leaving only water and oxygen and no residual hydrogen peroxide when the plasma is removed.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method for sterilizing a device having a diffusion restricted area and a non-diffusion restricted area comprising the steps of:

contacting the diffusion restricted area with a first liquid sterilant solution of a first concentration;

placing the device in a sterilization chamber;

introducing a second liquid sterilant solution of a second concentration into the sterilization chamber exterior of the diffusion restricted area, the second concentration being greater than the first concentration; and lowering the pressure of the chamber to vaporize the first and second liquid sterilant solutions and sterilize the diffusion restricted area and the non-diffusion restricted area of the instrument.

2. A method according to claim 1 wherein both of the first and second liquid sterilant solutions comprise hydrogen peroxide and water.

3. A method according to claim 2 wherein the concentration of hydrogen peroxide in the first liquid sterilant solution is less than 20 percent.

4. A method according to claim 3 wherein the concentration of hydrogen peroxide in the first liquid sterilant solution is less than 10 percent.

5. A method according to claim 2 wherein the concentration of hydrogen peroxide in the second liquid sterilant solution is greater than 40 percent.

6. A method according to claim 5 wherein the concentration of hydrogen peroxide in the second liquid sterilant solution is greater than 55 percent.

7. A method according to claim 1 wherein the pressure in the chamber is first lowered to a first pressure range for preferentially vaporizing the second liquid sterilant solution and then further lowered to a second lower pressure range for vaporizing the first liquid sterilant solution.

8. A method according to claim 1 wherein the pressure in the chamber is lowered below the vapor pressure of the second liquid sterilant solution.

9. A method according to claim 8 wherein the pressure in the chamber is lowered to 20 Torr or less.

10. A method according to claim 9 wherein the pressure in the chamber is lowered to 10 Torr or less and wherein the concentration of hydrogen peroxide in the first liquid sterilant solution is less than 10 percent and the concentration of hydrogen peroxide in the second liquid sterilant solution is greater than 45 percent.

11. A method according to claim 1 wherein the first and second concentrations are selected to allow the lowering of the chamber to a single pressure range which vaporizes the first liquid sterilant solution and second liquid sterilant solution simultaneously.

12. A method according to claim 11 wherein the single pressure range is less than the vapor pressure of the second liquid sterilant solution.

13. A method according to claim 12 wherein the single pressure range is 20 Torr or less.

14. A method according to claim 1 wherein the device is a medical instrument and the diffusion restricted area comprises a lumen therein.

15. A method according to claim 1 wherein the step of contacting the diffusion restricted area with a liquid sterilant solution comprises the step of condensing the liquid sterilant solution from a vapor inside the diffusion restricted area.

16. A method according to claim 1 wherein the step of contacting the diffusion restricted area with a liquid sterilant solution comprises the step of flowing a mist of said liquid sterilant solution into the diffusion restricted area.

17. A method according to claim 1 and further comprising the step of flowing air through the sterilization chamber to remove excess of the first liquid sterilant after the steps of contacting the diffusion restricted area with a first liquid sterilant solution and placing the device in a sterilization chamber, but prior to the step of lowering the pressure to vaporize the first and second liquid sterilant solutions.

18. A method according to claim 1 and further comprising the step of exciting the hydrogen peroxide into a plasma after the step of vaporizing.

19. A method according to claim 1 wherein the chamber pressure is allowed to rise after vaporizing the first liquid sterilant solution whereupon the pressure is lowered and the second liquid sterilant solution is introduced into the chamber.

* * * * *